United States Patent
Lee

(10) Patent No.: US 11,998,711 B2
(45) Date of Patent: Jun. 4, 2024

(54) MICRONEEDLE PATCH AND PRODUCTION METHOD THEREFOR

(71) Applicant: AMOLIFESCIENCE CO., LTD., Seoul (KR)

(72) Inventor: Jae Yeong Lee, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 1021 days.

(21) Appl. No.: 16/720,803

(22) Filed: Dec. 19, 2019

(65) Prior Publication Data

US 2020/0121901 A1 Apr. 23, 2020

Related U.S. Application Data

(62) Division of application No. 15/314,700, filed as application No. PCT/KR2015/005471 on Jun. 1, 2015, now abandoned.

(30) Foreign Application Priority Data

Jun. 2, 2014 (KR) .................. 10-2014-0066821

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 47/32* (2013.01);
(Continued)

(58) Field of Classification Search
CPC .... A61K 9/0021; A61M 37/0015; D01D 1/02
See application file for complete search history.

(56) References Cited

U.S. PATENT DOCUMENTS 6,611,707 B1 * 8/2003 Prausnitz .......... A61M 37/0015
604/21
2002/0045907 A1 4/2002 Sherman et al.
(Continued)

FOREIGN PATENT DOCUMENTS

KR 20070001886 1/2007
KR 1020070018410 2/2007
(Continued)

OTHER PUBLICATIONS

International Search Report—PCT/KR2015/005471 dated Aug. 26, 2015.

*Primary Examiner* — Robert S Walters, Jr.
*Assistant Examiner* — Andrew J Bowman
(74) *Attorney, Agent, or Firm* — CANTOR COLBURN LLP

(57) ABSTRACT

Provided are a micro-needle patch and a manufacturing method thereof. The micro-needle patch includes: a support on one surface of which grooves are formed; a gel membrane for delivery of a transmitter to be transferred in which the grooves are filled with a mixture of the transmitter with a biodradable resin, the mixture being in a gel phase; a plurality of micro-needles projected on the other surface of the support and for penetrating the skin; a first protective film that covers the gel membrane and is adhered on the support; and a second protective film that covers the plurality of micro-needles and is adhered on the other surface, wherein passages are formed by being penetrated from the support to each of the plurality of micro-needles or formed by penetrating the support between the plurality of micro-needles, so that the transmitter of the gel membrane is transferred to the skin.

14 Claims, 10 Drawing Sheets

(51) Int. Cl.
  *A61K 47/32* (2006.01)
  *B05D 1/04* (2006.01)
  *B29C 45/00* (2006.01)

(52) U.S. Cl.
  CPC ..... *A61M 37/00* (2013.01); *A61M 2037/0023* (2013.01); *A61M 2037/003* (2013.01); *A61M 2037/0038* (2013.01); *A61M 2037/0053* (2013.01); *A61M 2207/00* (2013.01); *B01D 2323/26* (2013.01); *B01D 2323/39* (2013.01); *B05D 1/04* (2013.01); *B29C 45/0001* (2013.01); *B29C 2045/0094* (2013.01)

(56) References Cited

U.S. PATENT DOCUMENTS

| | | | | |
|---|---|---|---|---|
| 2003/0017208 | A1* | 1/2003 | Ignatious | D01D 1/02 |
| | | | | 424/486 |
| 2003/0199812 | A1* | 10/2003 | Rosenberg | A61M 37/0015 |
| | | | | 604/47 |
| 2004/0106904 | A1 | 6/2004 | Gonnelli et al. | |
| 2006/0047242 | A1 | 3/2006 | Laurent et al. | |
| 2006/0195067 | A1* | 8/2006 | Wolter | A61K 9/0021 |
| | | | | 604/265 |
| 2007/0191761 | A1 | 8/2007 | Boone et al. | |
| 2009/0016935 | A1* | 1/2009 | Andrianov | A61K 9/0021 |
| | | | | 422/400 |
| 2009/0041810 | A1 | 2/2009 | Andrianov et al. | |
| 2011/0130706 | A1 | 6/2011 | Kellogg et al. | |
| 2012/0010529 | A1 | 1/2012 | Chickering, III et al. | |
| 2015/0209299 | A1 | 7/2015 | Xia et al. | |
| 2015/0306363 | A1 | 10/2015 | Meyer et al. | |

FOREIGN PATENT DOCUMENTS

| | | |
|---|---|---|
| KR | 100792640 | 1/2008 |
| KR | 101175326 | 8/2012 |
| KR | 101392947 | 5/2014 |

* cited by examiner

MICRONEEDLE PATCH AND PRODUCTION METHOD THEREFOR

TECHNICAL FIELD

The present invention relates to a micro-needle patch, and more particularly, to a micro-needle patch and a method of manufacturing the same, which forms a gel membrane for delivery of a transmitter to be transferred in which a drug or skin cosmetic treatment fluid is evenly distributed on the gel membrane by an electrospinning or electrospraying method, so that the drug or skin cosmetic treatment fluid is impregnated smoothly to the skin, and that quickly transfers the drug or skin cosmetic treatment fluid of the gel membrane to the skin via passages, to thereby improve a healing and skin cosmetic treatment effect of the skin.

BACKGROUND ART

Generally, micro-needle patches are spotlighted as a new concept drug injection technology with little pain. The micro-needle patches are a kind of a drug delivery system, and are attached on the skin to inject the drug or skin cosmetic treatment fluid inside the skin.

The micro-needle patches are used in medical and cosmetic treatment fields, which puncture the skin's stratum corneum to deliver active ingredients within the skin surface.

Here, the micro-needle is a fine needle to create a passage for directly penetrating through the skin layer and the dermal layer of the skin.

As such, the micro-needle patch enables an administration of the drug through the skin surface without a pain unlike a conventional injector type, and provides an easy use and a simple operation. Accordingly, researches on the micro-needle patches are diversely performed recently in the medical field.

Korea Patent Registration No. 10-1392947 discloses a micro-protrusions massage patch including a polymer material constituting micro-protrusions applicable to the skin of a living body and a common base of the micro-projections; and fibers of linear structures of a thickness of 0.1 µm to 100 µm dispersed in the polymer material. The massage patch causes no distortion in a drying step of a manufacturing process, maintains flexibility, and is not broken at the time of being bent or curved even after being manufactured, to thereby provide advantages of free shape changes and excellent breathes.

However, the massage patch disclosed in Korea Patent Registration No. 10-1392947 includes the micro-protrusions penetrating the skin in which the micro-protrusions contain a pharmaceutical agent, and are dissolved or melted to then infiltrate the skin to perform skin care and skin cosmetic treatment. Thus, since the amount of medicine to be injected into the skin depends on the size of the micro-projections, it is not so easy to increase the amount of medicine to be injected into the skin due to the size of the micro-projections, to thus cause an increase in production cost.

Thus, the present inventors have studied on techniques for improving properties of the micro-needle patches and found a structural and methodological feature that a production cost may be reduced by forming a gel membrane for delivery of a transmitter to be transferred into a thin film, in which a drug or skin cosmetic treatment fluid is evenly distributed on the gel membrane by an electrospinning or electrospraying method, so that the drug or skin cosmetic treatment fluid permeates smoothly into the skin, and by quickly transferring the drug or skin cosmetic treatment fluid of the gel membrane to the skin via passages, to thereby improve a healing and skin cosmetic treatment effect of the skin, and completed the present invention more economical, applicable, and competitive.

DISCLOSURE

Technical Problem

To solve the above problems or defects, it is an object of the present invention to provide a micro-needle patch that pierces the stratum corneum of the skin with micro-needles to form microholes, and infiltrates a transmitter to be transferred such as a drug or skin cosmetic treatment fluid from passages formed by penetrating the micro-needles from a support or passages formed by penetrating the support, into the microholes formed on the skin, and a method of manufacturing the same.

It is another object of the present invention to provide a micro-needle patch and a method of manufacturing the same, in which a production cost may be reduced by forming a gel membrane for delivery of a transmitter to be transferred into a thin film by using an electrospinning or electrospraying method.

It is still another object of the present invention to provide a micro-needle patch and a method of manufacturing the same, in which excellent process yield may be obtained and a manufacturing time may be shortened by forming a gel membrane for delivery of a transmitter to be transferred into a thin film in a plurality of supports, by using an electrospinning or electrospraying method.

Technical Solution

To accomplish the above and other objects of the present invention, according to an aspect of the present invention, there is provided a micro-needle patch comprising: a support on one surface of which grooves are formed; a gel membrane for delivery of a transmitter to be transferred in which the grooves is filled with a mixture of the transmitter with a biodradable resin, the mixture being in a gel phase; a plurality of micro-needles projected on the other surface of the support and for penetrating the skin; a first protective film that covers the gel membrane and is adhered on the support; and a second protective film that covers the plurality of micro-needles and is adhered on the other surface of the support, wherein passages are formed by penetrating each of the support and the plurality of micro-needles or formed by penetrating the support between the plurality of micro-needles, so that the transmitter of the gel membrane is transferred to the skin.

To accomplish the above and other objects of the present invention, according to another aspect of the present invention, there is provided a method of manufacturing a micro-needle patch, the method comprising the steps of: preparing a support on one surface of which a groove is formed and on the other surface of which a plurality of micro-needles are projected, and that covers the plurality of micro-needles, in which a needle protective film is adhered on the other surface of the support; preparing a spinning solution or a spraying solution by mixing a transmitter to be transferred, a biodradable resin, and a solvent; forming a gel membrane for delivery of the transmitter to be transferred, by electrospinning the spinning solution or electrospraying the spraying solution into the groove of the support; and adhering a protective film for protecting the gel membrane on the support.

Advantageous Effects

As described above, according to the present invention, a patch structure is implemented so that the skin is punctured into microholes by a plurality of micro-needles, and a drug or skin cosmetic treatment fluid can be injected inside the skin through passages, to thus carry out medication or a skin care.

Here, the passages are formed on each of the plurality of micro-needles, and the support, or are formed on the support, and the drug or skin cosmetic treatment fluid on the gel membrane for delivery of the transmitter to be transferred is quickly transferred to the skin through the passage, to thereby improve healing and skin cosmetic treatment effects.

Further, in the present invention, the gel membrane for delivery of the transmitter to be transferred is formed on the plurality of supports by a one-time electrospinning or electrospraying method, to thus obtain an excellent process yield and shorten a manufacturing time.

In addition, in the present invention, a gel membrane for delivery of a transmitter to be transferred is formed by filling a biodegradable resin that is formed by mixing a drug or skin cosmetic treatment fluid and a solvent into grooves of supports of a thin film form by electrospinning or electrospraying, to thereby remarkably reducing a manufacturing cost for healing and skin cosmetic treatment.

In addition, in the present invention, a drug or skin cosmetic treatment fluid that can be injected to the skin is evenly distributed on a gel membrane by an electrospinning or electrospraying method, so that the drug or skin cosmetic treatment fluid is impregnated smoothly to the skin.

BEST MODE

Hereinafter, a micro-needle patch and a method of manufacturing the same according to embodiments of the present invention will be described with reference to the accompanying drawings.

Figure 1:
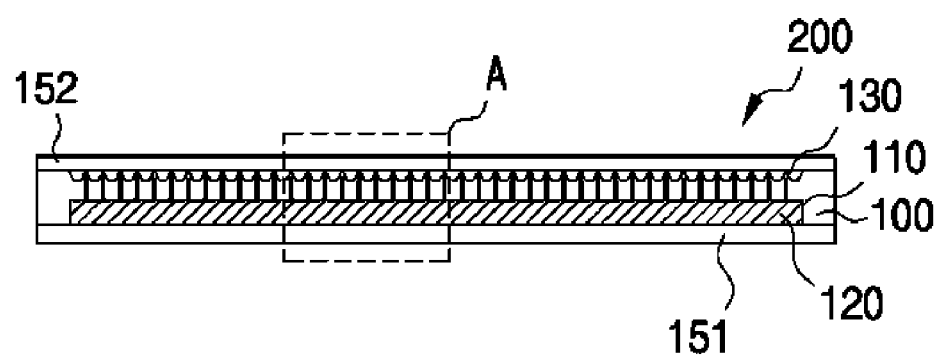
FIG. 1 is a schematic cross-sectional view of a micro-needle patch according to the invention.

FIG. 1 is a schematic cross-sectional view of a micro-needle patch according to the present invention.

Referring to FIG. 1, a micro-needle patch 200 according to the present invention includes a micro-needle patch comprising: a support 100 on one surface of which grooves 110 are formed; a gel membrane 120 for delivery of a transmitter to be transferred in which the grooves 110 are filled with a mixture of the transmitter with a biodradable resin, by an electrospinning or electrospraying method; a plurality of micro-needles130 projected on the other surface of the support 100 and for penetrating the skin to a certain depth; a first protective film 151 that covers the gel membrane 120 and is adhered on the support 100; and a second protective film 152 that covers the plurality of micro-needles 130 and is adhered on the other surface of the support 100, wherein passages (115 of FIG. 2) are formed by penetrating each of the support 100 and the plurality of micro-needles 130 or are formed by penetrating the support 100 between the plurality of micro-needles 130, so that the transmitter of the gel membrane is transferred to the skin.

According to the micro-needle patch 200 according to the present invention, a user peels off the second protective film 152, makes a plurality of micro-needles 130 come in contact with the skin, presses the first protective film 151, and then punctures the skin with the plurality of micro-needles 130, such that a drug or skin cosmetic treatment fluid of a gel membrane 120 for delivery of a transmitter to be transferred is quickly penetrated into holes of the punctured skin, to thereby improve healing or skin cosmetic treatment efficiency.

In this case, the drug or skin cosmetic treatment fluid of a gel membrane 120 is transferred to the skin through passages formed by being penetrated from the support 100 to each of the plurality of micro-needles 130 or passages formed by penetrating the support 100.

In the present invention, the micro-needle patch is attached on the skin with a predetermined thickness and thus protrudes from the skin. The protruding degree should be good by the aesthetic view, and thus the support 100 is preferably implemented in a thin film form.

Here, because the support 100 is in the form of a thin film, the depths of the grooves 100 become the shallower and thus the internal filling capacities of the grooves 100 become the smaller. Therefore, in the present invention, even if a small amount of a mixture of a drug or skin cosmetic treatment fluid and a biodegradable resin is injected into the grooves 110 having a small filling capacity, the grooves 110 may be fully filled with the small amount of the mixture, to thus reduce a manufacturing cost.

The support 100 is preferably implemented as a polymer material which is harmless to the human body, and it is preferable to use polyetherimide such as ULTEM® as the polymer material. Then, the support 100 is possibly implemented into shapes of the grooves 110 and the plurality of micro-needles 130 by an injection molding process.

A mold for molding the support 100 may be precisely manufactured by MEMS (Micro Electro Mechanical System).

The first and second protective films 151 and 152 enable secure storage and transfer for the micro-needle patch 200 and perform a function similar to a release film.

The first protective film 151 covers the gel membrane 120 for delivery of the transmitter to be transferred and is adhered to the support 100, such that the first protective film 151 has a function of preventing damage to the gel phase in the gel membrane 120 and a function of blocking penetration of foreign matters from the outside.

Then, the second protective film 152 covers each of the plurality of micro-needles 130 and is adhered to the other side of the support 100, to thereby protect the plurality of the micro-needles 130 from being bent or broken.

The support 100 is preferably formed of the plurality of micro-needles 130 in an integral form, and, in this case, the support 100 in which the grooves 110 and the plurality of micro-needles 130 are formed may be formed of a material that can be biodegradable or dissolved by human body fluids.

The material that is biodegradable or soluble includes one of polyethylene glycol (PEG), polyvinylpyrrolidone (PVP), polyvinyl alcohol (PVA), cellulose, hydroxypropyl cellulose (HPC), hydroxyethyl cellulose (HEC), hydroxypropylmethylcellulose (HPMC).

Meanwhile, the grooves 110 of the support 100 are filled with a mixture of a transmitter to be transferred and a biodegradable resin in a thin film to thus form the gel membrane 120.

Here, the gel membrane 120 is maintained in a gel phase in which the grooves 110 of the support 100 are filled with nanofibers or droplets formed by electrospinning or electrospraying a spinning solution or a spraying solution made of a mixture of a drug or a skin cosmetic treatment fluid with the biodradable resin.

The solvent used to prepare the spinning solution or spraying solution may employ alcohol that can be water-based spun and is harmless to the human body, and gelatin used in capsules formed by processing collagen extracted from cartilage etc., of animals may be applied as a modified embodiment of the biodegradable resin.

The drug may be a single drug or a mixed drug of anesthetics, narcotic vaccines, adjuvants, immunogens, immunomodulators, immune reagents, immune stimulants, analgesics, antibiotics, chitosans, collagens, gelatins, hyaluronic acids, polylactic acids, and polyglycolic acids. In this way, since the drug may be diffused into the body tissues or blood streams through the skin of a patient, to thus give a therapeutic effect to the patient.

The skin cosmetic treatment fluid is made of cosmetic ingredients such as essences for the skin care.

Figure 2:
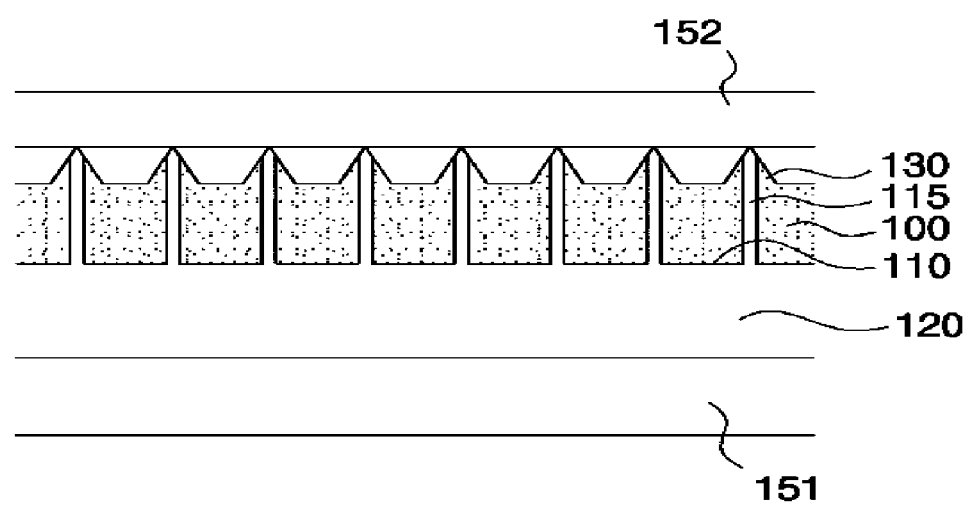
FIG. 2 is an enlarged view of a portion "A" in FIG. 1.
Figure 3A:
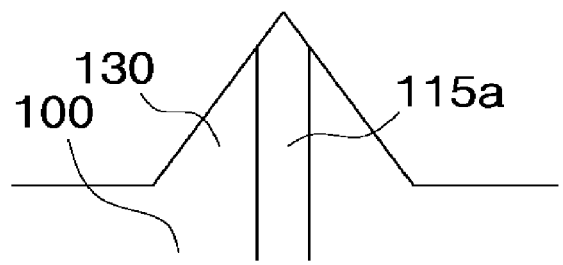
FIGS. 3A and 3B are schematic partial cross-sectional views for explaining a first modified example of a passage formed in the micro-needle patch according to the invention.
Figure 3B:
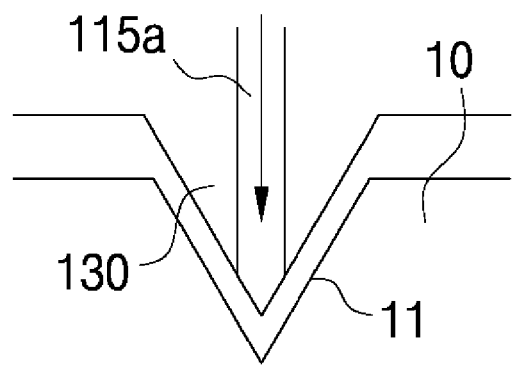
Figure 4A:
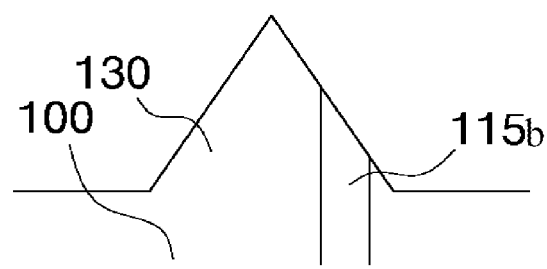
FIGS. 4A and 4B are schematic partial cross-sectional views for explaining a second modified example of a passage formed in the micro-needle patch according to the invention.
Figure 4B:
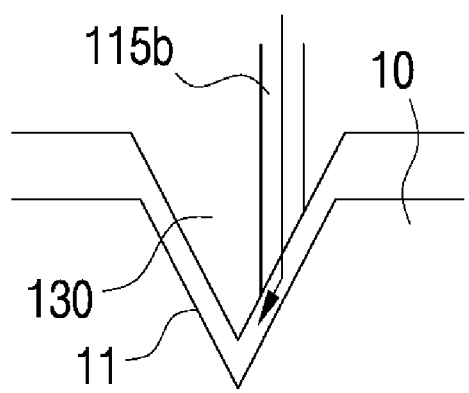
Figure 5A:
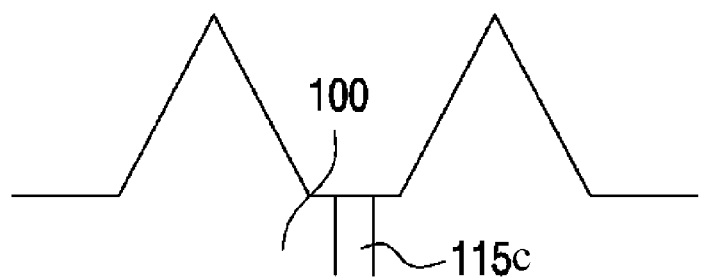
FIGS. 5A and 5B are schematic partial cross-sectional views for explaining a third modified example of a passage formed in the micro-needle patch according to the invention.
Figure 5B:
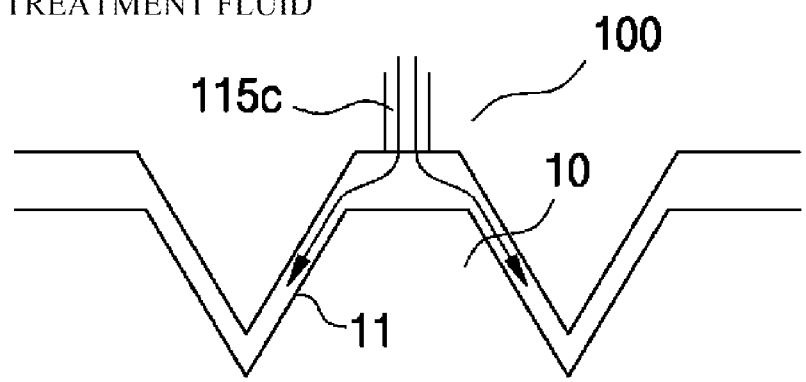

FIG. 2 is an enlarged view of a portion A in FIG. 1. FIGS. 3A and 3B are schematic partial cross-sectional views for explaining a first modified example of a passage formed in the micro-needle patch according to the invention. FIGS. 4A and 4B are schematic partial cross-sectional views for explaining a second modified example of a passage formed in the micro-needle patch according to the invention. FIGS. 5A and 5B are schematic partial cross-sectional views for explaining a third modified example of a passage formed in the micro-needle patch according to the invention.

Referring to FIG. 2, a plurality of micro-needles 130 are formed integrally with the support 100 in a micro-needle patch according to the present invention.

The second protective film 152 covers the plurality of micro-needles 130 and adhered to the other surface of the support 100, to protect the plurality of micro-needles 130, respectively.

The plurality of the micro-needles 130 are preferably designed as a height of micro-fine size. Here, the second protective film 152 may have a relatively large thickness. In addition, the second protective film 152 may be adhered on the other surface of the support in contact with the end of each of the plurality of micro-needles 130.

Therefore, the second protective film 152 covers each of the plurality of micro-needles 130 and is adhered to the other side of the support 100, to thereby protect the plurality of the micro-needles 130 from being bent or broken.

An adhesive (not shown) is formed in a region where the second protective film 152 and the support 100 are adhered. When the second protective film 152 is peeled off from the support 100, in order to operate micro-needle patch, the adhesive components of the adhesive remain in the region where the second protective film 152 and the support 100 are adhered to thus allow the micro-needle patch to be adhered onto the skin.

Thus, while a user peels off the second protective film 152 from the support 100 to allow the plurality of micro-needles 130 to be in contact with the skin, he or she presses the first protective film 151, to thus allow the plurality of micro-needles 130 to puncture the skin to be penetrated into the skin.

Meanwhile, the passages 115 to deliver a drug or skin cosmetic treatment fluid of the gel membrane 120 filled into the grooves 110 of the support 100 are formed by penetrating the support 100.

In this case, the passages 115 may be formed into any one of a structure (115a of FIG. 3A) formed by penetrating the respective centers of the support and the plurality of micro-needles, a structure (115b of FIG. 4A) formed by penetrating the respective side walls of the support 100 and the plurality of micro-needles 130, and a structure (115c of FIG. 5A) formed by penetrating the support 100 between the plurality of micro-needles 130, or a combination of these structures.

When holes 11 are formed in the skin 10 by means of the micro-needles 130, the passages 115 having such a structure deliver the gel-phase drug or the skin cosmetic treatment fluid of the gel membrane through the holes 11 formed in the skin 10.

Figure 6:
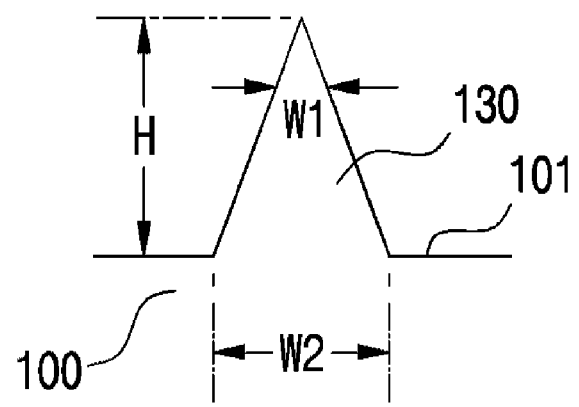
FIG. 6 is a schematic partial cross-sectional view for explaining a shape of the micro-needle patch according to the invention.

FIG. 6 is a schematic partial cross-sectional view for explaining a shape of a micro-needle patch according to the present invention.

Referring to FIG. 6, a micro-needle 130 is configured so that width (W1) of an upper region thereof is preferably narrower than width (W2) of a lower region thereof, relative to a surface 101 of a support 100 to penetrate the skin. Here, ends of the plurality of micro-needles 130 may be sharp or round.

Thus, the micro-needles 130 can penetrate the stratum corneum of the skin, so that a drug or skin cosmetic treatment fluid can be injected into a predetermined area inside the skin through the passages.

Here, when the plurality of micro-needles 130 drill the stratum corneum of the skin so that a drug or skin cosmetic treatment fluid can be injected into a predetermined area (e.g., dermal) inside the skin, occurrence of bleeding should be avoided. Accordingly, preferably, the height (H) of each of the micro-needles 130 is less than 1000 μm, and may be designed as several micrometers to a few hundreds of micrometers.

The plurality of micro-needles 130 are formed of a material that is biodegradable or soluble by a human body fluid inside the skin so that side effects are not caused when the plurality of micro-needles 130 are penetrated into the internal skin. Here, the plurality of micro-needles 130 may be biodegradable or soluble within a short time of several seconds or for a long time in units of several hours. In addition, the material of the plurality of micro-needles 130 may also be a resin harmless to the human body.

Therefore, the present invention implements a patch structure through which a drug or skin cosmetic treatment fluid can be injected into a predetermined area inside the skin, through holes formed by the micro-needles via passages formed in at least one of the support and the micro-needles, to thus provide an advantage capable of improving the healing and skin cosmetic treatment efficiency.

Figure 7:
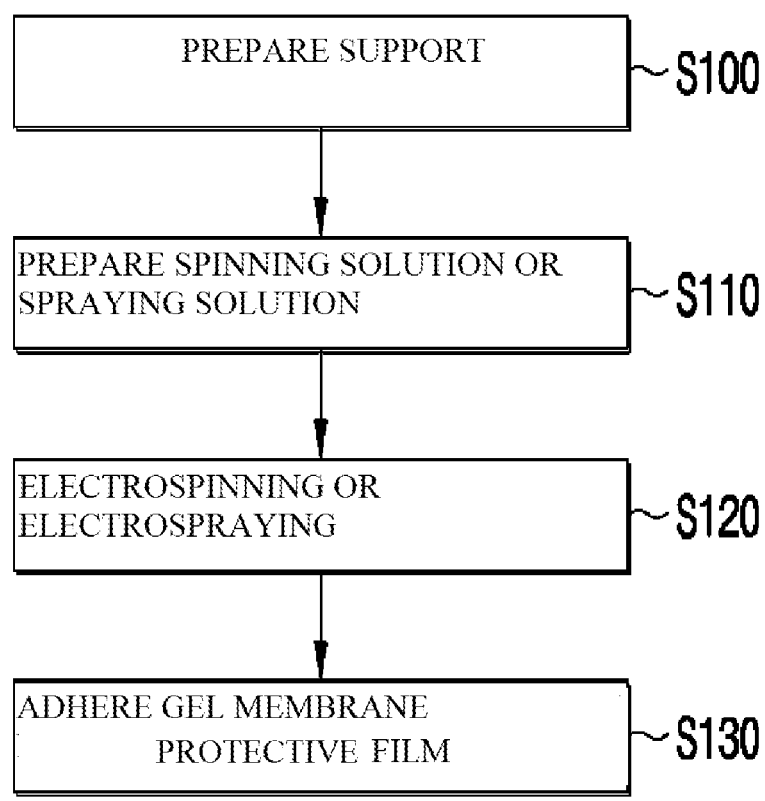
FIG. 7 is a flowchart view of a method of manufacturing a micro-needle patch according to the invention.
Figure 8:
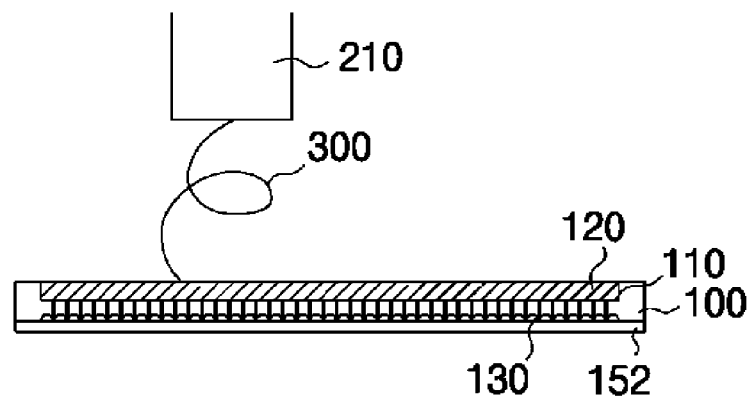
FIG. 8 is a schematic cross-sectional view for explaining a method of manufacturing a micro-needle patch by electrospinning in accordance with the present invention.
Figure 9:
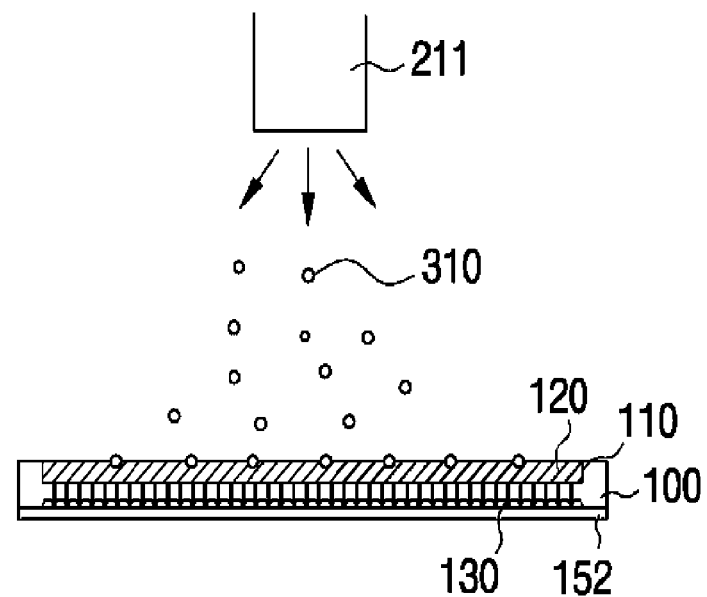
FIG. 9 is a schematic cross-sectional view for explaining a method of manufacturing a micro-needle patch by electrospraying according to the invention.

FIG. 7 is a flowchart view of a method of manufacturing a micro-needle patch according to the invention. FIG. 8 is a schematic cross-sectional view for explaining a method of manufacturing a micro-needle patch by electrospinning in accordance with the present invention. FIG. 9 is a schematic cross-sectional view for explaining a method of manufacturing a micro-needle patch by electrospraying according to the invention.

In the present invention, a mixture of a drug or skin cosmetic treatment fluid with a biodegradable resin is electrospun or electrosprayed on a support to thus prepare a micro-needle patch.

That is, referring to FIG. 7, in order to produce the micro-needle patch, a support is first prepared (S100), in which grooves are formed on one surface of the support, and a plurality of micro-needles are protruded from the other surface of the support, and, a needle protective film to cover the plurality of micro-needles, is adhered on the other side of the support. Then, the drug or skin cosmetic treatment fluid, and a solvent are mixed with a biodegradable resin to thus prepare a spinning solution or spraying solution (S110).

Then, a gel membrane for delivery of a transmitter to be transferred is formed by electrospinning the spinning solution or electrospraying the spraying solution, into the grooves of the support (S120).

Then, the gel membrane is wrapped with a gel membrane protective film to then be adhered on the support (S130).

Here, the gel membrane protective film is a first protective film, and the needle protective film is a second protection film.

A process of performing an electrospinning method will be described as follows. As shown in FIG. 8, the drug or skin cosmetic treatment fluid, and a solvent are mixed with a biodegradable resin to thus prepare a spinning solution, and then the spinning solution is electrospun. In this case, nanofibers 300 are spun from a spinning nozzle 210, to then be accumulated into the grooves 110 of the support 100, and the gel membrane 120 is formed in the inside of the grooves 110 with the accumulated nanofibers 300.

In addition, as shown in FIG. 9, a process of performing an electrospraying method is accomplished by electrospraying a spraying solution in a spraying nozzle 211, in which the spraying solution is made of a mixture of the drug or skin cosmetic treatment fluid, and a solvent with a biodegradable resin. In this case, droplets 310 are discharged from a spraying nozzle 211, and the droplets 310 are accumulated into the grooves 110 of the support 100, to thus form the gel membrane 120.

As described above, the nanofibers 300 or droplets 310 are filled in the grooves 110 of the support 100 to thus complete the gel membrane 120 to then end the electrospinning, or the support 100 is made to escape from a region at which the spraying solution is sprayed from the spraying nozzle 210. Then, the gel membrane protective film surrounding the gel membrane 120 is adhered on the support 100.

As described above, in the present invention, the electrospun or electrosprayed nanofibers or droplets are accumulated in the grooves 110 of the support 100, to thus form a gel membrane 120 to thereby remarkably reduce a production cost of a patch for healing and skin cosmetic treatment.

In addition, there is an advantage that the drug or the skin cosmetic treatment fluid is permeated into the skin by forming a gel membrane in which the drug or the skin cosmetic treatment fluid that can be impregnated in the skin through electrospinning or electrospraying is evenly distributed.

Figure 10:
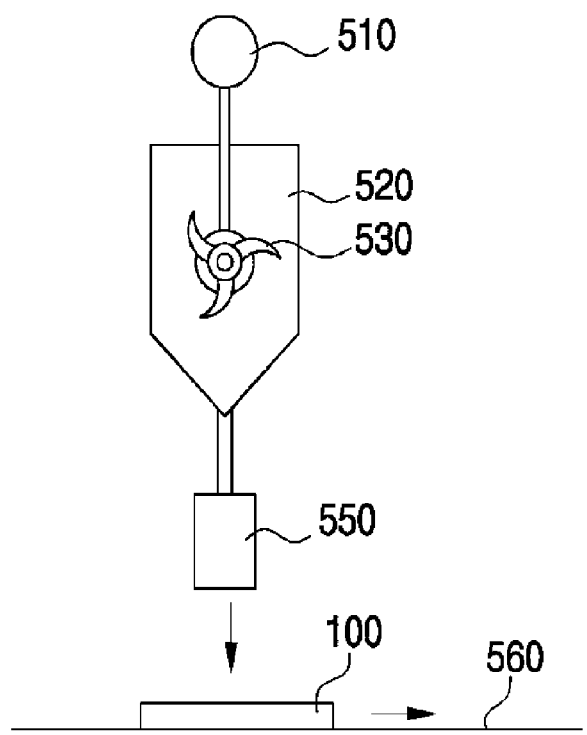
FIG. 10 is a schematic diagram of an electrospinning or electrospraying apparatus applied to the present invention.

FIG. 10 is a schematic diagram of an electrospinning or electrospraying apparatus that is applied to the present invention.

Referring to FIG. 10, the electrospinning or electrospraying apparatus includes a solution tank 520 in which a spinning liquid that is formed of a mixture of a drug or skin cosmetic treatment fluid, and a solvent with a biodegradable resin is stored, and a nozzle 550 to which a high voltage generator (not shown) is connected.

The nozzle 550 is disposed on an upper side of a grounded conveyor type collector 560 moving at a constant speed. Here, a plurality of the nozzles 550 may be disposed along a travelling direction (in the horizontal direction of an arrow mark) of the collector 560, and the solution tank 520 may be built with a stirrer 530 using a mixing motor 510 as a driving source.

The spinning solution or spraying solution sequentially discharged from the nozzle 550 is electrospun to discharge ultra-fine nanofibers, or is electrosprayed to discharge droplets (in the vertical direction of an arrow mark), while passing through the nozzle 550 charged by a high voltage generator, and the nanofibers or droplets are sequentially accumulated in the grooves 110 (of FIG. 9) of the support 100 on a grounded conveyor type collector 560 moving at a constant speed, to thus form a gel membrane 120.

Figure 11:
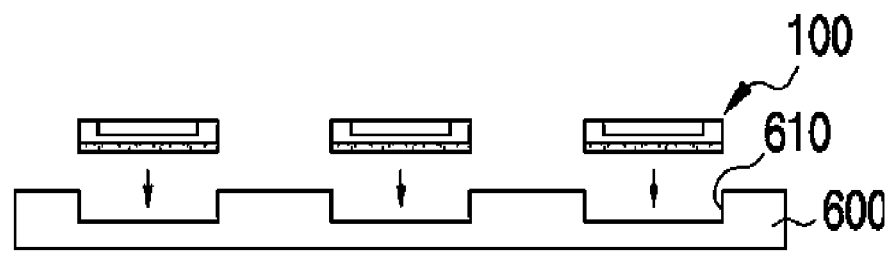
FIG. 11 is a schematic cross-sectional view of a support seat tray that can be applied to a method of manufacturing a micro-needle patch according to the invention.
Figure 12:
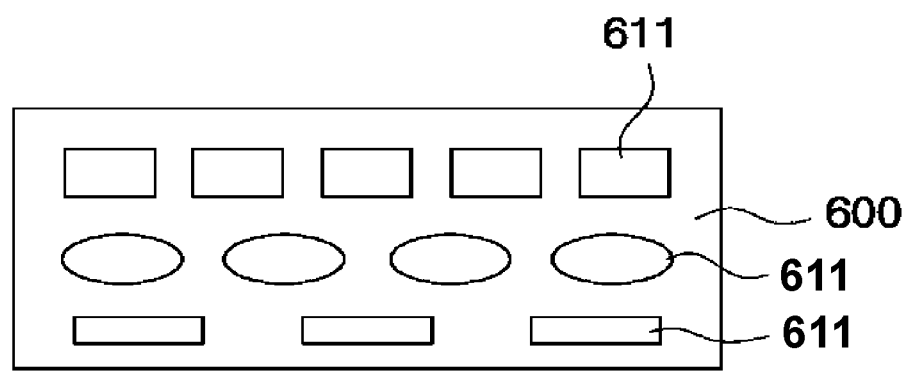
FIG. 12 is a schematic plan view illustrating a modification of the support seat tray of FIG. 11.
Figure 13:
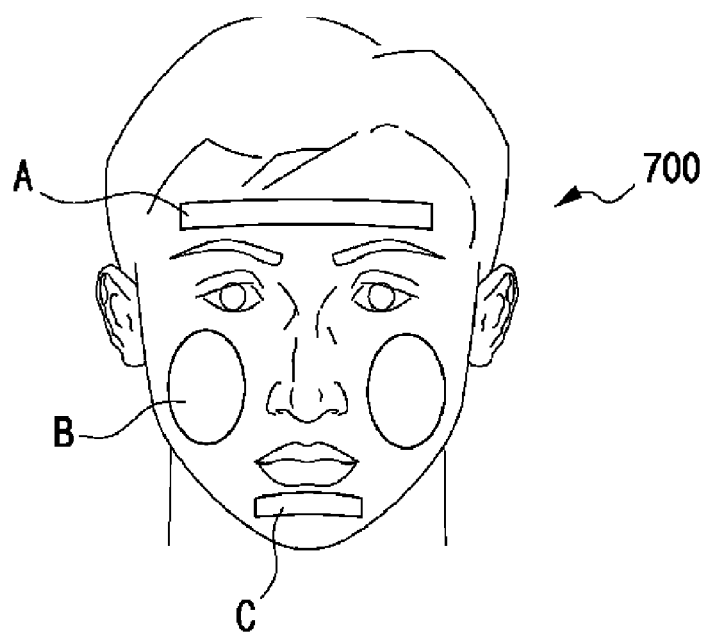
FIG. 13 is a view for explaining a modification of using the micro-needle patch prepared by using the support seat tray shown in FIG. 12.

FIG. 11 is a schematic cross-sectional view of a support seat tray that can be applied to a method of manufacturing a micro-needle patch according to the invention. FIG. 12 is a schematic plan view illustrating a modification of the support seat tray of FIG. 11. FIG. 13 is a view for explaining a modification of using the micro-needle patch prepared by using the support seat tray shown in FIG. 12.

Referring to FIG. 11, in the present invention, a plurality of supports 100 are inserting into receiving portions 610 of a tray 600, to then perform an electrospinning or electrospraying process.

That is, a plurality of supports 100 are inserted into the receiving portions 610 of the tray 600 and placed on the collector 560 of the electrospinning or electrosparying apparatus of FIG. 10. Then, nanofibers or droplets discharged from an electrospinning nozzle or an electrospraying nozzle 550 are accumulated in grooves of a plurality of supports 100. Accordingly, gel membranes may be formed on the plurality of supports 100 through a one-time electrospinning or electrospraying process.

In addition, according to the present invention, as shown in FIG. 12, a plurality of receiving portions 611 whose sizes are different from one another are formed on the tray 600 and a plurality of supports whose sizes are different from one another are inserted into the plurality of receiving portions 611. Accordingly, gel membranes may be formed on the plurality of supports 100 through a one-time electrospinning or electrospraying process.

Accordingly, according to the present invention, the gel membranes may be formed on the plurality of supports 100 through a one-time electrospinning or electrospraying process, to thus obtain an excellent process yield and shorten a manufacturing time.

As described above, when micro-needle patches whose sizes are different from each other are produced, as shown in FIG. 13, patches may be operated in various regions A, B, and C whose sizes are different from one another on the face of a person 700.

As described above, the present invention has been described with respect to particularly preferred embodiments. However, the present invention is not limited to the above embodiments, and it is possible for one who has an ordinary skill in the art to make various modifications and variations, without departing off the spirit of the present invention. Thus, the protective scope of the present invention is not defined within the detailed description thereof but is defined by the claims to be described later and the technical spirit of the present invention.

INDUSTRIAL APPLICABILITY

The present invention relates to a drug delivery system (DDS), and may be applied to a micro-needle patch that can effectively inject a transmitter such as a drug or skin cosmetic treatment fluid into the inner skin at a low cost.

The invention claimed is:

1. A method of manufacturing a micro-needle patch, the method comprising:
    forming a support inserted into a receiving portion in a tray, the support having a first surface and a second surface opposite the first surface, wherein the support includes: a plurality of supports each inserted into the receiving portion in the tray;
    forming a plurality of micro-needles projecting from the first surface of the support;
    forming a first passage from the support to each of the micro-needles or a second passage from the support between two neighboring micro-needles;
    forming a groove in the second surface of the support,
    electrospinning a spinning solution into the groove to form nanofibers, the spinning solution comprising a transmitter to be transferred, a biodegradable resin, and a solvent;
    accumulating the nanofibers in the groove to form a gel membrane for delivery of the transmitter to be transferred,
    adhering a first protective film on the gel membrane to protect the gel membrane; and
    adhering a second protective film on the first surface of the support to cover the micro-needles.

2. The method of claim 1, wherein the plurality of supports differ from one another in size.

3. The method according to claim 1, wherein the first passage is formed at a center of the each of the micro-needles.

4. The method according to claim 1, wherein the support comprises polyetherimide.

5. The method according to claim 1, wherein the support comprises a material that is biodegradable or soluble by a human body fluid.

6. The method according to claim 5, wherein the material comprises polyethylene glycol, polyvinylpyrrolidone, polyvinyl alcohol, cellulose, hydroxypropyl cellulose, hydroxyethyl cellulose, or hydroxypropylmethylcellulose.

7. The method according to claim 1, wherein a width of an upper region of the micro-needles is narrower than a width of a lower region relative to the first surface of the support.

8. The method according to claim 1, wherein a height of the micro-needles is less than 1000 μm.

9. The method according to claim 1, wherein the transmitter comprises at least one selected from the group consisting of anesthetics, narcotic vaccines, adjuvants, immunogens, immunomodulators, immune reagents, immune stimulants, analgesics, antibiotics, chitosans, collagens, gelatins, hyaluronic acids, polylactic acids, polyglycolic acids, and a mixture thereof.

10. The method according to claim 1, wherein the transmitter comprises a skin cosmetic treatment fluid.

11. The method according to claim 1, wherein the second passage is formed at a side wall of the each of the micro-needles.

12. A method of manufacturing a micro-needle patch, the method comprising:
    forming a support inserted into a receiving portion in a tray, the support having a first surface and a second surface opposite the first surface, wherein the support includes: a plurality of supports each inserted into the receiving portion in the tray;
    forming a plurality of micro-needles projecting from the first surface of the support;
    forming a first passage from the support to each of the plurality of micro-needles or a second passage from the support between two neighboring micro-needles;
    forming a groove in the second surface of the support,
    electrospraying a spraying solution into the groove to form droplets, the spraying solution comprising a transmitter to be transferred, a biodegradable resin, and a solvent;
    accumulating the droplets in the groove to form a gel membrane for delivery of the transmitter to be transferred,
    adhering a first protective film on the gel membrane to protect the gel membrane; and
    adhering a second protective film on the first surface of the support to cover the micro-needles.

13. The method of claim 12, wherein the plurality of the supports differ from one another in size.

14. The method according to claim 12, wherein the support comprises a material that is biodegradable or soluble by a human body fluid.

* * * * *